United States Patent [19]

Rubinstein

[11] 4,456,590

[45] Jun. 26, 1984

[54] HEAT TREATMENT OF LYOPHILIZED BLOOD CLOTTING FACTOR VIII CONCENTRATE

[75] Inventor: Alan Rubinstein, Houston, Tex.

[73] Assignee: Cedars Sinai Medical Center, Los Angeles, Calif.

[21] Appl. No.: 377,863

[22] Filed: May 13, 1982

Related U.S. Application Data

[63] Continuation-in-part of Ser. No. 317,513, Nov. 2, 1981, which is a continuation of Ser. No. 205,913, Nov. 12, 1980, abandoned.

[51] Int. Cl.$^3$ ............................................. A61K 35/16
[52] U.S. Cl. ..................................................... 424/101
[58] Field of Search .......................................... 424/101

[56] References Cited

U.S. PATENT DOCUMENTS

| | | |
|---|---|---|
| 3,041,242 | 6/1962 | Barr et al. |
| 3,100,737 | 8/1963 | Auerswald et al. |
| 3,859,168 | 1/1975 | Barth et al. |
| 4,250,139 | 2/1981 | Luck et al. |
| 4,297,344 | 10/1981 | Schwinn et al. |
| 4,327,086 | 4/1982 | Fukushima et al. ................. 424/105 |
| 4,347,259 | 8/1982 | Suzuki et al. |

FOREIGN PATENT DOCUMENTS 1471336  4/1977  United Kingdom .

OTHER PUBLICATIONS

De Flora, J. of Immunol, vol. 120, No. 1, (Jan. 1978), pp. 40–45.
De Flora, Chem. Abst., vol. 88, (1978), p. 61,042d.
Kaplan, "The Heat Inactivation of Vaccinia Virus," J. Gen. Microbiol., 18:58–63, (1958).
Cowdery et al., "Stability Characteristics of Freeze–Dried Human Live Virus Vaccines," Develop. Biol. Standard, 36:297–303, (1977).
Beardmore et al., "Preservation of Influenza Virus Infectivity by Lyophilization," Applied Microbiology, 16(2):362–365, (1968).
Greiff et al., "Stability of Suspensions of Influenza Virus Dried to Different Contents of Residual Moisture by Sublimation in Vacuo," Applied Microbiology, 16(6):835–840, (1968).
Plowright et al., "Studies on Rinderpest Culture Vaccine. III. Stability of the Lyophilised Product," Res. Vet. Sci., 11:71–81, (1970).
Apostolov et al., "Selective Inactivation of the Infectivity of Freeze-Dried Sendai Virus by Heat," Cytobiology, 10:255–259, (1973).
Schable et al., "Stability of a Reference Panel of Lyophilized Hepatitis B Antigens and Antibodies," J. Biol. Standardization, 7:293–299, (1979).
Berge et al., "Preservation of Enteroviruses by Freeze-Drying," Applied Microbiology, 22(5):850–853, (1971).
Grieff et al., "An Accelerated Storage Test for Predicting the Stability of Suspensions of Measles Virus Dried by Sublimation in Vacuo," J. Immunology, 94(3):395–400, (1965).
Kraft et al., "Lyophilization of Poliomyelitis Virus. Heat Inactivation of Dry MEF1 Virus," Proc. Soc. Exp. Biol. Med., 9:306–309, (1954).
Scatchart et al., "Chemical, Clinical, and Immunological Studies on the Products of Human Plasma Fractionation. IV. A Study of the Thermal Stability of Human Serum Albumin," J. Clin. Invest., 23:445–453, (1944).
Sirridge, *Laboratory Evaluation of Hemostatis*, Second Edition, Lea & Febiger, Philadelphia, 1974, pp. 7–8.
Bangham et al., "Stability of Some Clotting Factors in Freeze–Dried Factor VIII–Reference Plasma and Concentrate," Chem. Abstracts, 76:22760u, (1972).
Brozovic et al., "Stability of Prothrombin and Factor VII in Freeze-Dried Plasma," J. Clin. Path., 24:690–693, (1971).
*Plasma Products; Use and Management. A Technical Workshop*, Kolins et al., (eds.), The Committee on Technical Workshops, American Association of Blood Banks, Anaheim, CA, (1982).
Gerety et al., "Plasma Derivatives and Viral Hepatitis," Transfusion, 22(5):347, (1982).
Tabor et al., *Infectious Complications of Blood Transfusion*, Academic Press, New York, 1982, pp. 6, 24.
Aronson et al., "Historical and Future Therapeutic Plasma Derivatives (Epilogue)," Seminars in Thombosis and Hemostasis, VI(2):121–123, (1980).
Rosenberg et al., "Thermoinactivation of Virus of Botkin's Disease (Hepatite Virus) in Dry Fibrinogen and Albumin Preparations," *XII International Congress on Blood Transfusion Abstracts*, MIR Publishers, Moscow, 1969, pp. 473–475.
Soulier et al., "Prevention of Virus B Hepatitis (SH Hepatitis)," Amer. J. Dis. Child, 123:429–434, (1972).
Paine et al., "Human Albumin Infusions and Homologous Serum Jaundice," JAMA, 150(3):199–202, (1952).
Havens et al., "Properties of the Etiologic Agent of Infectious Hepatitis," Proc. Soc. Exp. Biol. Med., 58:203–204, (1945).
Bertrand et al., "Clinical Investigations with a Heat–Treated Plasma Protein Fraction-Plasmanate," Vox Sang., 4:385–402, (1959).
Roberts et al., "Post-Transfusion Hepatitis Following the Use of Prothrombin Complex Concentrates," Thrombos, Diathes. Haemorrh., (Stuttg.), 33:610–616, (1975).
Tabor et al., "Removal of Hepatitis-B-Virus Infectivity from Factor–IX Complex by Hepatitis-B Immune–Globulin," The Lancet, pp. 68–70, Jul. 12, 1980.
Allen et al., "Homologous Serum Jaundice and Its Relation to Methods of Plasma Storage," Jama 144(13):1069–1074, Nov. 25, 1950.
Funakoshi et al., "Injectable Inactivated Vaccine Against Hepatitis B," Chem Abstracts, 89:65254t, (1978).
Schwinn et al., "Blood Coagulation Factors," Chem. Abstracts, 94:36335t, (1981).

*Primary Examiner*—Sam Rosen
*Attorney, Agent, or Firm*—Lyon & Lyon

[57] ABSTRACT

A method for treating blood products to eliminate hepatitis virus present therein is disclosed. Blood products treated according to the method are first lyophilized and then subjected to heat for a period of time sufficient to inactivate the hepatitis virus. At the conclusion of the heating step the blood product can be reconstituted using sterile water or a like diluent. No adverse effects on blood product activity following treatment have been observed. The method has special applicability to blood plasma fractions such as Factor VIII, Factor IX and fibrinogen.

4 Claims, No Drawings

HEAT TREATMENT OF LYOPHILIZED BLOOD CLOTTING FACTOR VIII CONCENTRATE

RELATED APPLICATIONS

This application is a continuation-in-part of application Ser. No. 317,513 filed Nov. 2, 1981, which is in turn a continuation of application Ser. No. 205,913 filed Nov. 12, 1980, now abandoned.

TECHNICAL FIELD

The present invention relates generally to methods for heat treating plasma fractions and is particularly directed to a series of steps whereby various plasma fractions may be heated in lyophilized form for the purpose of inactivating hepatitis virus present in the fractions.

BACKGROUND ART

Utilization of clotting factor concentrates obtained from fractionated blood plasma for the purpose of intervening therapeutically with respect to inherited bleeding disorders such as hemophilia is severely compromised as a consequence of the inordinate risk posed to the hemophiliac patient by the presence of hepatitus virus in the concentrates. For example, commercial Factor VIII and IX concentrates are typically employed to increase the clotting ability of a hemophilia victim's blood, but these concentrates are prepared from pools of plasma contributed by thousands of donors and contain the inherent hepatitis risk of a like number of single unit transfusions. As McCullen and Zuckerman have shown, see *Journal of Medical Virology*, Vol. 8, No. 29 (1981), despite stringent screening of individual donors for hepatitis B surface antigens (HBsAg), such plasma pools clearly transmit both hepatitis B and non-A, non-B hepatitis.

Hepatitis transmission by albumin and other heat-stable plasma components unrelated to blood coagulation has heretofore been prevented by heating the plasma components in solution at temperatures of 60° C. for ten hours. Similar attempts to heat clotting factor concentrates in solution, by way of contrast, have been shown to markedly reduce or eliminate clotting factor activity in the concentrates and thus do not appear to offer a viable solution to the problem of hepatitis transmission associated with conventional hemophiliac therapy. More recently, highly purified Factor VIII precipitate has been dissolved in a solution of sucrose glycine and heated for ten hours at 60° C. Although the Factor VIII concentrate subsequently derived from the heated precipitate does retain clotting factor activity, the yields obtained using this approach are very low, e.g., about 8%. See Heimburger, et al., Hemostasis, Vol. 10 (supplement 1), p. 204 (1981) and Heimburger, et al., Blut, Vol. 20, p. 129 (1981). As a net result, the prior art to date does not furnish any means for effectively inactivating hepatitis virus present in clotting factor concentrates nor does the prior art teach a means for preventing the transmission of hepatitis virus to patients undergoing therapy with clotting factor concentrates.

DISCLOSURE OF THE INVENTION

It is therefore an object of the present invention to provide a method for heat treating clotting factor concentrates to inactivate any hepatitis virus present therein without reducing clotting factor activity.

It is another object of the present invention to provide a method for heat treating clotting factor concentrates to inactivate any hepatitis virus present therein, which method results in substantial yields of concentrate without significant reduction of clotting factor activity in the concentrate.

It is still another object of the present invention to provide a method for heat treating clotting factor concentrates wherein the concentrates are first prepared in lyophilized form to enhance the stability of the concentrates during the heating process.

It is a further object of the present invention to provide a method for heat treating lyophilized plasma fractions to produce a vaccine effective against both hepatitis B virus and non-A, non-B hepatitus virus.

These and other objects of the present invention are achieved by lyophilizing either whole plasma or plasma fractions such as Factor VIII concentrate, Factor IX concentrate, fibrinogen and cryoprecipitate and thereafter subjecting the lyophilized whole plasma or plasma fractions to elevated temperatures for varying periods of time.

BEST MODE FOR CARRYING OUT THE INVENTION

The ability to isolate clotting factors present in human blood has been indispensable in understanding the pathology of hemophilia and other inherited bleeding disorders. Concommitantly, the discovery of plasma fractionation schemes for obtaining practical quantities of clotting factor concentrates has enabled medical science to utilize the clotting factor concentrates as therapeutic tools in treating bleeding disorders. Transfusion therapy employing Factor VIII and Factor IX concentrates in particular has proven quite successful in ministering to hemophiliac patients. Unfortunately, the risk of hepatitis transmission due to the large number of plasma donors required for commercial production of clotting factors concentrates remains as the one serious drawback associated with transfusion therapy. A typical plasma fractionation scheme, disclosed in *Seminars in Thrombosis and Hemostasis*, Vol. VI, No. 1, p. 4 (1979), yields cryoprecipitate and supernate, the former fraction constituting a source of both Factor VIII concentrate and fibrinogen and the latter fraction constituting a source of Factor IX concentrate in addition to Factors II, VII, and X concentrates. As Gerety and Eyster have demonstrated in "Hepatitis Among Hemophiliacs", *Non-A, Non-B Hepatitis*, p. 103–106 (1981), hepatitis B virus initially present in whole plasma is distributed to the Factor VIII and Factor IX derivatives during the plasma fractionation process. As also demonstrated by Maynard and Bradley, "Transmission by Blood Products", *Non-A, Non-B Hepatitis*, p. 78–79 (1981), non-A, non-B hepatitis exists in both Factor VIII and Factor IX derivatives. Previous attempts to heat-treat clotting factor concentrates in solution for the purpose of inactivating hepatitis virus have been ineffective. The development of techniques for lyophilizing clotting factor derivatives, however, has opened a new avenue of exploration with regard to stabilizing clotting factor derivatives during the heat treating process, in turn establishing a means for inactivating hepatitis virus present in the clotting factor derivatives without destroying clotting factor activity.

TEST PROCEDURES FOR VERIFYING RETENTION OF CLOTTING FACTOR ACTIVITY

Paired samples of various lyophilized plasma fractions, each such pair having identical lot numbers, were received from several manufacturers. The samples generally weighed less than 100 g and were packaged in vials having volumes of 60 ml to 90 ml. One sample in each pair was heated, either by placing the sample vial in a water bath or dry oven at a predetermined temperature under room pressure for a predetermined period of time, or by placing the lyophilized material itself in a dry oven without the vial present. The remaining sample in each pair served as a control and was refrigerated at 4°-6° C. during the heat-treating process. Following heat treatment, both the control and heat-treated lyophilized samples were reconstituted with sterile water. Reconstitution was generally carried out according to manufacturer's specifications, although the solubility of some heat-treated samples was markedly improved by increasing the amount of sterile water used during reconstitution over that recommended by the manufacturer. In vitro Factor VIII and Factor IX assays were performed using a one-stage manual fibrometer method at dilutions ranging between 1:40 and 1:400 to obtain a measure of Factor VIII and Factor IX clotting activity. In vitro recovery of fibrinogen following reconstitution of both the control and heat-treated lyophilized fibrinogen samples was measured in a similar fashion. In some of the experiments, reconstituted plasma fractions were observed for light transmission at 580 nm in a Beckman Model 25 Spectrophotometer. Agarose gel electrophoresis with an ICL immunoelectrophoresis plate was carried out for several of the Factor VIII and Factor IX paired samples, using goat anti-human serum supplied by Hyland Diagnostics as a standard. The plates were specifically electrophoresed by a Buchler power supply set at 25 ma for 35 minutes. Upon completion of the electrophoresis, the plates were incubated in antisera for 18 to 24 hours and examined under indirect light. Panagell electrophoresis with a Worthington Diagnostics plate was carried out on additional paired samples of Factor VIII concentrate, using a Biorad water-cooled electrophoresis cell.

Further in vitro experiments were performed by heating lyophilized samples of Factor VIII concentrate in a water bath at room pressure and at predetermined temperatures for predetermined periods of time. Factor $VIII_{Ag}$ was then determined using the method described by Laurell, "Electroimmuno Assay," *The Scandinavian Journal of Clinical and Laboratory Investigation*, Vol. 29, pp. 21–37 (1972). Factor VIII results were calculated for dilutions of 1:40, 1:80, 1:100 and 1:200 by plotting the height of the rockets of the Laurell standard curve against the percentage of dilution. Unknowns were expressed as a percentage of normal, based on the rocket heights of the unknowns in the standard curve.

In vivo recovery of clotting factor activity for both heat-treated Factor VIII and Factor IX concentrates was measured by injecting reconstituted, heat-treated lyophilized Factor VIII and Factor IX concentrates respectively into hemophilia A and hemophilia B dogs. A heat-treated, lyophilized Factor IX concentrate was also injected into a control dog. Laboratory parameters including Hct, serum protein, WBC, platelet count, blood smear, respiration rate, body temperature, pulse and clotting factor activity were subsequently ascertained for each of the animals at various intervals following the injections.

Results of the in vitro testing performed on Factor VIII concentrate are summarized in Tables I and II:

TABLE I

Measurements of Clotting Factor Activity Following Heat-Treatment of Lyophilized Factor VIII Concentrate

| Lot | Temp. | Time | Dilution | % Activity |
|---|---|---|---|---|
| *A C-1081 | Control | — | 1:20 | Approximately |
| " | " | — | 1:40 | 10% decrease in |
| " | " | — | 1:80 | activity was |
| " | 60° C. | 10 hr. | 1:20 | observed for |
| " | " | " | 1:40 | heat-treated |
| " | " | " | 1:80 | samples relative to the control. |
| A NC-8247 | Control | — | 1:40 | 1438 |
| " | " | — | 1:80 | 1697 |
| " | 62°-64° C. | 16.33 hr. | 1:40 | 1215 |
| " | " | " | 1:80 | 1360 |
| B AHF-355 | Control | — | 1:40 | 1912 |
| " | " | — | 1:80 | 1600 |
| " | " | — | 1:160 | 1312 |
| " | 64° C. | 20 hr. | 1:40 | 1080 |
| " | " | " | 1:80 | 1072 |
| " | 74° C. | 17 hr. | 1:40 | 1144 |
| " | " | " | 1:80 | 1024 |
| " | " | " | 1:160 | 864 |
| " | 76° C. | 17 hr. | 1:40 | 1040 |
| " | " | " | 1:80 | 976 |
| B 347 | Control | — | 1:100 | 1180 |
| " | " | — | 1:200 | 1000 |
| " | 83° C. | 24 hr. | 1:100 | 100 |
| " | " | " | 1:200 | 100 |
| " | 85° C. | 24 hr. | 1:100 | <1 |
| " | 95° C. | 7 hr. | 1:100 | <1 |
| " | 97° C. | 7.5 hr. | 1:200 | <1 |
| C AJ-0470 | Control | — | 1:100 | 912 |
| " | 75° C. | 20 hr. | 1:100 | 2076 |
| C AJ-1080 | Control | — | 1:200 | 2080 |
| " | " | — | 1:400 | 1920 |
| " | 80° C. | 24 hr. | 1:200 | 1380 |
| " | " | " | 1:400 | 1360 |
| C AJ-1120 | Control | — | 1:40 | 2800 |
| " | " | — | 1:80 | 2032 |
| " | 78° C. | 21 hr. | 1:40 | 1592 |
| " | " | " | 1:80 | 1392 |
| " | 80° C. | 20 hr. | 1:40 | 1176 |
| " | " | " | 1:80 | 1600 |
| " | 90° C. | 12 hr. | — | Clotted Specimen |
| " | 100° C. | 1.5 hr. | 1:40 | 1248 |
| " | " | " | 1:80 | 1264 |
| C AJ-1150 | Control | — | 1:40 | 2176 |
| " | " | — | 1:80 | 2480 |
| " | " | — | 1:100 | 1870 |
| " | " | — | 1:200 | 2080 |
| " | 65° C.** | 26.33 hr. | 1:40 | 1592 |
| " | 65° C.** | " | 1:80 | 1520 |
| " | 83° C. | 24 hr. | 1:100 | 730 |
| " | " | " | 1:200 | 620 |
| " | 85° C. | 24 hr. | 1:100 | 1000 |
| " | " | " | 1:200 | 1160 |
| " | 90° C. | 10 hr. | 1:40 | 1032 |
| " | " | " | 1:80 | 1056 |
| " | 95° C. | 7 hr. | — | Clotted Specimen |
| " | 97° C. | 7.5 hr. | 1:100 | 80 |
| " | " | " | 1:200 | 100 |
| " | 100° C. | 10 hr. | 1:40 | 88 |
| " | " | " | 1:80 | 48 |
| C AJ-1160 | Control | — | 1:100 | 3680 |
| " | " | — | 1:200 | 3420 |
| " | " | — | 1:400 | 3200 |
| " | 78° C. | 24 hr. | 1:100 | 2420 |
| " | " | " | 1:200 | 1520 |
| " | " | " | 1:400 | 1440 |
| " | 78° C. | 24 hr. | 1:200 | 1720 |
| " | " | " | 1:400 | 1680 |
| " | 80° C. | 22 hr. | 1:200 | 1400 |
| " | " | " | 1:400 | 1360 |
| " | 100° C. | 7 hr. | 1:200 | 1760 |
| " | " | " | 1:400 | 1760 |

TABLE I-continued

Measurements of Clotting Factor Activity Following
Heat-Treatment of Lyophilized Factor VIII Concentrate

| Lot | Temp. | Time | Dilution | % Activity |
|---|---|---|---|---|
| C Al-2120 | Control | — | 1:100 | 816 |
| " | 110° C.*** | 1.5 hr. | 1:100 | 18 |
| C Al-2531 | Control | — | 1:200 | 3500 |
| " | " | — | 1:400 | 2700 |
| " | 85° C. | 20 hr. | 1:200 | 46 |
| " | " | " | 1:400 | 43 |

Note:
All times and temperatures are approximate. Following heat treatment at higher temperatures, amounts of sterile water in excess of manufacturer's recommendations were added to some concentrates until solubilization was visually confirmed.
*A lots were manufactured by Cutter Laboratories; B lots were manufactured by Michigan Red Cross; C lots were manufactured by Alpha Therapeutics.
**Heat-treated in a dry oven (sample removed from vial).
***Heat-treated in a dry oven (sample contained in vial).

TABLE II

Determination of Factor VIII$_{Ag}$ Following
Heat-Treatment of Lyophilized Factor VIII Concentrate

| Lot | Temp | Time | Dilution | Rocket Height (mm) | % Ag |
|---|---|---|---|---|---|
| B AHF-355 | Control | — | 1:40 | 35 | 3720* |
| " | " | — | 1:80 | 22 | 4080 |
| " | 64° C. | 20 hr. | 1:40 | 39 | 4240 |
| " | " | " | 1:80 | 26 | 5120 |
| " | 74° C. | 17 hr. | 1:40 | 40 | 4400 |
| " | " | " | 1:80 | 26 | 5120 |
| C Al-1120 | Control | — | 1:100 | 15 | 4700 |
| " | 90° C. | 12 hr. | 1:100 | 0 | 0 |
| C Al-1150 | Control | — | 1:200 | 13 | 7200 |
| " | 83° C. | 24 hr. | 1:200 | 12 | 6200 |
| " | 85° C. | 24 hr. | 1:200 | 15 | 9400 |
| " | 97° C. | 7.5 hr. | 1:200 | 0 | 0 |

Note:
All times and temperatures are approximate. Following heat treatment at higher temperatures, amounts of sterile water in excess of manufacturer's recommendations were added to some concentrates until solubilization was visually confirmed.
*B lots were manufactured by Michigan Red Cross; C lots were manufactured by Alpha Therapeutics.

Results from the testing of Factor IX concentrate are summarized in Table III:

TABLE III

Measurements of Clotting Factor Activity Following
Heat-Treatment of Lyophilized Factor IX Concentrate

| Lot | Temp. | Time | Dilution | % Activity |
|---|---|---|---|---|
| *A 9-C0044 | Control | — | 1:40 | 616 |
| " | " | — | 1:80 | 1200 |
| " | " | — | 1:200 | 2400 |
| " | " | — | 1:400 | 3520 |
| " | 100° C. | 4 hr. | 1:40 | 520 |
| " | " | " | 1:80 | 1104 |
| " | 100° C. | 12 hr. | 1:200 | 1680 |
| " | " | " | 1:400 | 2480 |
| " | 110° C.** | 13 hr. | 1:400 | 1640 |
| " | 110° C.** | " | 1:800 | 2560 |
| " | 122° C.** | 12 hr. | 1:200 | 340 |
| " | 122° C.** | " | 1:400 | 480 |
| " | 132° C.** | 12 hr. | 1:200 | 12 |
| " | 132° C.** | " | 1:400 | 24 |
| A NC9055 | Control | — | n/a | 2600 |
| " | 100° C. | 0.5 hr. | n/a | 2350 |

Note:
All times and temperatures are approximate. Following heat treatment at higher temperatures, amounts of sterile water in excess of manufacturer's recommendations were added to some concentrates until solubilization was visually confirmed.
*A lots manufactured by Cutter Laboratories.
**Heat treated in a dry oven.

Results of the testing performed on fibrinogen concentrate are summarized in Table IV:

TABLE IV

Recovery of Fibrinogen Following Heat-Treatment
of Fibrinogen Concentrate in Lyophilized Form

| Lot | Temp. | Time | Dilution | Recovery (mg/dl) |
|---|---|---|---|---|
| *D-003678 | Control | — | 1:20 | 400 |
| " | " | — | 1:40 | 680 |
| " | 60° C. | 10-11 hr. | 1:20 | 660 |
| " | " | " | 1:40 | 680 |
| " | Control | — | 1:10 | 195 |
| " | " | — | 1:20 | 760 |
| " | " | — | 1:40 | 700 |
| " | 60° C. | 10 hr. | 1:10 | 105 |
| " | " | " | 1:10 | 225 |
| " | " | " | 1:20 | 250 |
| " | 60° C. | 17 hr. | 1:10 | 190 |
| " | " | " | 1:20 | 220 |
| *E | Control | — | 1:40 | 1280 |
| " | " | — | 1:80 | 1280 |
| " | 60° C. | 10 hr. | 1:40 | 1520 |
| " | " | " | 1:80 | 1320 |
| " | 60° C. | 10 hr. | 1:40 | 1860 |
| " | " | " | 1:80 | 1520 |
| " | 65° C. | 10 hr. | 1:40 | 1640 |
| " | " | " | 1:80 | 1400 |
| " | " | 23 hr. | 1:40 | 1420 |
| " | " | " | 1:80 | 1320 |
| " | Control | — | 1:40 | 1048 |
| " | " | — | 1:80 | 1064 |
| " | 100° C. | 3 hr. | 1:40 | 788 |
| " | " | " | 1:80 | 784 |
| " | 254° F.** | 3 hr. | 1:5 | 133 |

Note:
All times and temperatures are approximate. Following heat treatment at higher temperatures, amounts of sterile water in excess of manufacturer's recommendations were added to some concentrates until solubilization was visually confirmed.
*D lots manufactured by Cal Biochem; E lots manufactured by Kabi.
**Heat-treated in a dry oven (sample contained in vial).

DISCUSSION OF SELECTED TEST RESULTS

The results summarized in Tables I–IV can be combined to provide a relative indication of clotting activity retention and fibrinogen recovery in lyophilized plasma fractions subjected to the heat-treatment process of the present invention. More particularly, the percentage activity or measured recovery at various dilutions of reconstituted Factor VIII, Factor IX and fibrinogen concentrates can be averaged for individual control samples and compared with similarly-averaged percentage activity or measured recovery in corresponding paired samples of heat-treated Factor VIII, Factor IX and fibrinogen concentrate. Where such comparisons are made, it can be seen, for example, that lyophilized Factor VIII concentrate obtained from one manufacturer (Lot No. A C-1081) and heated at 60° C. for 10 hours retained greater than 90% of its in vitro Factor VIII clotting activity in comparison to an unheated control. The reconstituted, heat-treated Factor VIII concentrate further exhibited an absorbance of 0.30 at 580 nm in comparison to an absorbance of 0.20 for the unheated control, and showed no differences relative to the unheated control following immunoelectrophoresis with the goat anti-human serum. Reconstituted Factor VIII concentrates from a different lot (Lot. No. A NC-8247) of the same manufacturer, which had been heated in lyophilized form at 62°–64° C. for approximately 16 hours and then stored at 6° C. for seven days, showed greater than 80% recovery of Factor VIII clotting activity in comparison to an unheated control. An overall increase in anodal migration relative to the unheated control was noted following immunoelectrophoresis against goat anti-human serum.

In similar fashion, lyophilized Factor VIII concentrate obtained from a second manufacturer (Lot No. C Al-1120), when heated at approximately 78° C. for 21 hours, showed 62% in vitro retention of clotting activity upon reconstitution as compared to an unheated control. Reconstituted Factor VIII concentrate from the same lot of the second manufacturer, after heat treatment in lyophilized form for 20 hours at approximately 80° C., still retained 57% in vitro clotting activity as compared to an unheated control, whereas reconstituted Factor VIII from the same lot of the second manufacturer, which had previously been heated in lyophilized form for one and one-half hour at approximately 100° C., retained approximately 52% in vitro clotting activity as compared to an unheated control. When a different lot (Lot No. C Al-1150) of lyophilized Factor VIII concentrate from the second manufacturer was heat-treated in accordance with the present invention, in vitro recoveries of clotting activity in comparison to the unheated control ranged from 67% for 26 hours and 20 minutes of heat treatment at 65° C. to 34% for 24 hours of heat treatment at 83° C. to 55% for 24 hours of heat treatment at 85° C. Measurements of Factor VIII antigen for the two samples of Factor VIII concentrate heat-treated at 83° C. and 85° C. respectively showed a 15% loss and no loss in antigen levels. It should also be noted that greatly improve solubilization of the latter sample of heat-treated Factor VIII concentrate was achieved by adding between 50 ml and 75 ml of sterile water to the sample rather than the 25 ml recommended by the manufacturer.

Heat treatment of lyophilized Factor VIII samples obtained from a third manufacturer (Lot No. AHF-355) confirmed results observed for the first two manufacturers. That is, heat treatment of the third manufacturer's lyophilized Factor VIII concentrate for 20 hours at 64° C. yielded clotting activity recovery of 61% in comparison to an unheated control, heat treatment of the same concentrate for 17 hours at 74° C. yielded clotting activity recovery of 63% and heat treatment of the same concentrate for 17 hours at 76° C. yielded clotting activity recovery of 57%. Factor VIII antigen levels in the reconstituted samples heated at 64° C. and 74° C. showed no decrease when compared to the unheated control level.

A sample of lyophilized Factor IX concentrate obtained from the first manufacturer (Lot No. A 9-C0044) and immersed in a water bath at 100° C. for 20–30 minutes yielded essentially full in vitro recovery of clotting activity when compared to an unheated control. Factor II and Factor VII both appeared stable 2 hours following reconstitution of the heat-treated sample, while Factor X decreased approximately 20% within 6 days of reconstitution. Absorbance measurements obtained 2 hours after reconstitution yielded values of 0.006 to 0.007 at 580 mm for both control and heat-treated samples. No visual difference could be detected between the heat-treated concentrate and the unheated control following immunoelectrophoresis of the Factor IX concentrate against goat anti-human serum. Additional samples of Factor IX concentrate from the first manufacturer, which were respectively heat-treated in lyophilized form at 100° C. for 12 hours and at 110° C. for 13 hours, also showed full recovery of Factor IX clotting activity, although complete solubilization of the latter sample required 40 ml to 60 or greater ml of sterile water as opposed to the manufacturer's recommended 20 ml. The data from Table III thus suggests that Factor IX concentrate in lyophilized form is largely heat stable for 4 hours at temperatures between 100° C.–110° C.

A sample of lyophilized fibrinogen concentrate obtained from a fourth manufacturer (Lot No. D-003678) and heat-treated for 11 hours at 60° C. showed no in vitro loss of fibrinogen when compared with an unheated control. A sample of lyophilized fibrinogen concentrate obtained from the same manufacturer, when heat-treated for 17 hours at 60° C., showed a fibrinogen recovery of 97% compared with the unheated control. Samples of lyophilized fibrinogen concentrates obtained from a fifth manufacturer (Lot E), when heated for 10 and 23 hours respectively at 60° C. and 65° C., showed no in vitro loss of fibrinogen relative to the unheated control, while a sample of lyophilized fibrinogen concentrate from the fifth manufacturer showed 74% fibrinogen recovery compared to the control following heat treatment for 3 hours at 100° C.

As previously indicated, in vivo testing of heat-treated Factor VIII and Factor IX concentrates was carried out using hemophilia A or Factor VIII deficient and hemophilia B or Factor IX deficient dogs. The hemophilia A dog received reconstituted Factor VIII concentrate which had previously been heat-treated in lyophilized form at 60° C. for 10 hours, while the hemophilia B dog received reconstituted Factor IX concentrate which had previously been heat-treated at 100° C. for 3 to 4 hours. Results of the in vivo testing are reported in Tables V and VI below.

TABLE V

F-VIII Deficient Dog Given Heat Treated Factor VIII Concentrate

|   | HCT % | Protein gm % | WBC/ mm$^3$ | Platelets/ mm$^3$ | FVIII RA %* | FVIII C %* | Temp °F. | Respiration | Pulse |
|---|---|---|---|---|---|---|---|---|---|
| PRE | 44 | 6.1 | 3,795 | 330,000 | 106 | <2 (1-2) | 100.0 | 48 | 132 |
| Infusion |  |  | 20 ml given in 3.5 min |  |  | 400° |  |  |  |
| 15 min | 45 | 5.9 | 3,190 | 110,000 | 151 | 12 | 102.3 | 42 | 138 |
| 90 min | 47 | 6.0 | 6,050 | 165,000 | n = 2 156, 159 | 12 | 101.0 | pant | 108 |
| 3 hours | 44 | 6.1 | 5,115 | 231,000 | 168 | 15 | 100.9 | pant | 108 |
| 5 hours | 43 | 6.0 | 4,785 | 165,000 | 159 | 9 | 100.5 | 30 | 114 |
| 7.5 hours | 44 | 5.9 | 3,245 | 198,000 | 150 | 9 | 101.0 | 42 | 108 |

TABLE VI

F-IX Deficient Dog Given Heat Treated Factor IX Concentrate

| | HCT % | Protein gm % | WBC/ mm$^3$ | Platelets/ mm$^3$ | Trombin clot time sec | FVIII C %* | F-IX %* | Temp °F. | Respiration | Pulse |
|---|---|---|---|---|---|---|---|---|---|---|
| PRE | 43 | 5.5 | 5,840 | 187,000 | 5.5 | 67 | <1 (0-5-1) | 101.5 | 36 | 150 |
| Infusion | | | 20 ml given in 3 min. | | | 5* | 524* | | | |
| 15 min | 42 | 5.6 | 5,005 | 429,000 | 5.5 | 47 | 9 | 101.8 | 30 | 150 |
| 90 min | 44 | 5.8 | 6,545 | 253,000 | 5.5 | 59 | 10 | 102.0 | 48 | 144 |
| 3 hours | 40 | 5.7 | 8,910 | 429,000 | 6.0 | 39 | 6 | | 42 | 162 |
| 5 hours | 41 | 5.8 | 5,610 | 231,000 | 6.0 | 64 | 6 | 100.3 | 42 | 126 |
| 7.5 hours | 44 | 5.7 | 6,985 | 363,000 | 5.5 | 95 | 4 | 101.0 | 36 | 162 |

The results reported in Table V amply illustrate the marked increase in Factor VIII clotting activity for a hemophilia A dog following injection of heat-treated Factor VIII concentrate. Similarly, the results reported in Table VI amply illustrate the Factor IX recovery observed in a hemophilia B dog following injection of heat-treated Factor IX concentrate. The apparent absence of physiological stress or other adverse reaction as seen from the data in Tables V and VI suggests that Factor VIII and Factor IX concentrates which have been processed according to the steps of the present invention remain biologically acceptable.

It has now been demonstrated that plasma fractions such as Factor VIII and Factor IX concentrates of varying purity can be safely heat-treated in lyophilized form at elevated temperatures for extended periods of time without significantly destroying the clotting activity of the concentrates. It has further been demonstrated that plasma fractions such as fibrinogen of varying purity can be safely heat-treated in lyophilized form at elevated temperatures for extended periods of time without destroying the recoverability of the fibrinogen. Visual observations confirm that the solubility of lyophilized Factor VIII, Factor IX and fibrinogen concentrates is not deleteriously affected by heat-treatment inasmuch as the amount of sterile water added to the lyophilized concentrate samples during reconstitution can simply be increased until complete solubility is achieved. Consequently, through suitable adjustment of the heating temperature, length of heating and purity levels involved, hepatitis virus of both the B type and the non-A, non-B type can be inactivated in plasma fractions while maintaining the viability and therapeutic integrity of the fractions. Given the additional fact that hepatitis B virus and probably non-A, non-B hepatitis virus are preferentially distributed in the clotting factor fractions, i.e., in Factor VIII and Factor IX concentrates, heat treatment of the clotting factor fractions in lyophilized form at suitable temperatures for suitable periods of time can also serve to render the hepatitis virus immunogenic as well as non-infectious. As a consequence, reconstituted heat-treated lyophilized Factor VIII and Factor IX concentrates can function as hepatitis vaccines while simultaneously providing the therapeutic benefits otherwise associated with clotting factor fractions.

It should, moreover, be apparent from extrapolation of the test results reported in Tables I-VI that the method of the present invention can be performed at essentially any point during the plasma fractionation process. That is, at any point along the fractionation process where a plasma derivative can be lyophilized, heat treatment of the plasma derivative can be performed and the derivative resolubilized or reconstituted prior to continuation of the fractionation process. Thus, for example, where Factor VIII concentrate is ultimately derived from a plasma fractionation scheme such as that disclosed in Mammen, et al., "Treatment of Bleeding Disorders with Blood Components," *Reviews of Hematology*, Vol. 1, p. 144 (1980), cryoprecipitate obtained from fresh frozen plasma, clarified extract obtained from cryoprecipitate and supernatant obtained from clarified extract can all be lyophilized and heat-treated in the same manner as the Factor VIII concentrate itself. Selection of an appropriate point in the plasma fractionation scheme for applying the heat treatment can then be based on pragmatic considerations such as cost or convenience.

Several embodiments of the present invention have been illustrated hereinabove. It is to be understood, however, that various modifications to the temperature ranges, heating periods and purity levels set forth in conjunction with the aforementioned embodiments can be made by those skilled in the art without departing from the scope and spirit of the present invention. It is therefore the intention of the inventor to be bounded only by the limits of the following claims.

I claim:

1. A method for treating blood clotting Factor VIII concentrate in order to minimize the effect of any hepatitis virus present in the blood clotting Factor VIII concentrate, said method comprising the steps of:
   lyophilizing the blood clotting Factor VIII concentrate, followed by;
   heating the lyophilized blood clotting Factor VIII concentrate at a predetermined temperature of at least about 60° C. for a period of time sufficient to render hepatitis virus present in the blood clotting Factor VIII concentrate non-infectious, said heating generally decreasing as said predetermined temperature is increased.

2. The method claimed in claim 1 wherein said predetermined temperature is between about 60° C. and about 100° C.

3. The method claimed in claim 1 wherein said predetermined temperature is between about 60° C. and about 125° C.

4. The method claimed in claim 1 further comprising: adding sterile water to the lyophilized blood Factor VIII concentrate following completion of said heating step until solubilization of the lyophilized blood clotting Factor VIII concentrate is achieved.

* * * * *

REEXAMINATION CERTIFICATE (1063rd)
United States Patent [19]
Rubinstein

[11] B2 4,456,590
[45] Certificate Issued    May 30, 1989

[54] HEAT TREATMENT OF LYOPHILIZED BLOOD CLOTTING FACTOR VIII CONCENTRATE

[75] Inventor: Alan Rubinstein, Houston, Tex.

[73] Assignee: Cedars Sinai Medical Center, Los Angeles, Calif.

Reexamination Request:
No. 90/001,553, Jul. 14, 1988

Reexamination Certificate for:
Patent No.: 4,456,590
Issued: Jun. 26, 1984
Appl. No.: 377,863
Filed: May 13, 1982

Reexamination Certificate B1 4,456,590 issued Feb. 26, 1984.

Related U.S. Application Data

[63] Continuation-in-part of Ser. No. 317,513, Nov. 2, 1981, which is a continuation of Ser. No. 205,913, Nov. 12, 1980, abandoned.

[51] Int. Cl.$^4$ .................... A61K 37/00; A61K 35/14
[52] U.S. Cl. ........................................ 514/2; 424/101
[58] Field of Search ............................ 514/2; 424/101

[56] References Cited
PUBLICATIONS

Rozenberg et al, "Hemostatic Human Blood Fractions For Transfusion: Antihemophiliac Plasma, Antihemophiliac Globulin, and Fibrinogen", Probelmy Gematologi i Perelivaniya Krovi, vol. 8, No. 6, pp. 3–6 (1963), (Translation enclosed herewith from Translation Supplement, Federation Proceedings, vol. 23, No. 2, Part. II, pp. T322–T325 (1964).

Rosenberg et al, "On the Thermoinactivation of Botkin's Hepatitis Virus in Dry Fibrinogen and Albumin Preparations", Proc 12th Congr. Int. Soc. Blood Transf., Moscow, 1969, Bibl. Haemat., No. 38, Part II, pp. 474–478, (Karger, Basel 1971).

*Primary Examiner*—Sam Rosen

[57] ABSTRACT

A method for treating blood products to eliminate hepatitis virus present therein is disclosed. Blood products treated according to the method are first lyophilized and then subjected to heat for a period of time sufficient to inactiviate the hepatitis virus. At the conclusion of the heating step the blood product can be reconstituted using sterile water or a like diluent. No adverse effects on blood product activity following treatment have been observed. The method has special applicability to blood plasma fractions such as Factor VIII, Factor IX and fibrinogen.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–4 is confirmed.

* * * * *